United States Patent
Yamada et al.

(10) Patent No.: US 8,900,462 B2
(45) Date of Patent: Dec. 2, 2014

(54) METHOD FOR REMOVING LEUKOCYTE AND FILTER FOR USE THEREIN

(75) Inventors: Yukihiro Yamada, Oita (JP); Yukihiko Uchi, Shizuoka (JP)

(73) Assignee: Asahi Kasei Medical Co., Ltd, Tokyo (JP)

( * ) Notice: Subject to any disclaimer, the term of this patent is extended or adjusted under 35 U.S.C. 154(b) by 837 days.

(21) Appl. No.: 11/569,901

(22) PCT Filed: Jun. 9, 2005

(86) PCT No.: PCT/JP2005/010555
§ 371 (c)(1),
(2), (4) Date: Dec. 1, 2006

(87) PCT Pub. No.: WO2005/120600
PCT Pub. Date: Dec. 22, 2005

(65) Prior Publication Data
US 2008/0011691 A1  Jan. 17, 2008

(30) Foreign Application Priority Data
Jun. 9, 2004  (JP) ................. 2004-171815

(51) Int. Cl.
*B01D 37/00* (2006.01)
*B01D 61/00* (2006.01)
*C02F 1/00* (2006.01)
*B01D 39/16* (2006.01)
*A61M 1/36* (2006.01)

(52) U.S. Cl.
CPC ......... *B01D 39/1623* (2013.01); *A61M 1/3633* (2013.01); *A61M 2202/0439* (2013.01)

USPC ........... 210/767; 210/335; 210/491; 210/483; 210/488; 210/507; 604/6.09

(58) Field of Classification Search
CPC ................ A61M 1/3633; A61M 2202/0439; B01D 39/1623
USPC ............................... 210/510.1, 767
See application file for complete search history.

(56) References Cited

U.S. PATENT DOCUMENTS 4,701,267 A * 10/1987 Watanabe et al. ............ 604/6.09
5,164,087 A    11/1992 Naoi et al.
(Continued)

FOREIGN PATENT DOCUMENTS

JP    60-193468    10/1985
JP    63-175157    7/1988
(Continued)

OTHER PUBLICATIONS

Machine Translation of WO2004/050146, Dec. 2003, WIPO, Kimura et al. 604/6.03.*

(Continued)

*Primary Examiner* — Dirk Bass
(74) *Attorney, Agent, or Firm* — Greenblum & Bernstein, P.L.C.

(57) ABSTRACT

A leukocyte-removing filter, characterized in that it comprises a filter material having a vertical permeation coefficient (kx) of $0.5 \times 10^{-12}$ to $2.0 \times 10^{-12}$ m$^2$ and a ratio (ky/kx) of a horizontal permeation coefficient (ky) to kx of 0.5 to 1.5; and a method for removing leukocytes using said filter. The above leukocyte-removing filter has a higher leukocyte-removing performance per unit volume and also does not bring clogging nor increase of pressure drop.

26 Claims, 3 Drawing Sheets

(56) References Cited

U.S. PATENT DOCUMENTS

| | | | |
|---|---|---|---|
| 5,476,587 A * | 12/1995 | Kuroki et al. | 210/496 |
| 5,478,470 A | 12/1995 | Fukuda et al. | |
| 5,665,233 A | 9/1997 | Fukuda et al. | |
| 5,707,520 A | 1/1998 | Kuroki et al. | |
| 6,241,886 B1 * | 6/2001 | Kitagawa et al. | 210/507 |
| 6,267,898 B1 | 7/2001 | Fukuda et al. | |
| 2004/0104165 A1 * | 6/2004 | Oishi et al. | 210/490 |
| 2006/0184085 A1 * | 8/2006 | Kimura et al. | 604/6.03 |

FOREIGN PATENT DOCUMENTS

| | | |
|---|---|---|
| JP | 1-224324 | 9/1989 |
| JP | 2-203909 | 8/1990 |
| JP | 7-124255 | 5/1995 |
| JP | 10-057477 | 3/1998 |
| JP | 63-175157 | 3/1998 |
| JP | 11-012182 | 1/1999 |
| WO | 93/03740 | 3/1993 |
| WO | WO2004/050146 * | 12/2003 ... 604/6.03 |
| WO | WO 2004/050146 | 6/2004 |

OTHER PUBLICATIONS

U.S. Appl. No. 10/537,252, filed 2006.
U.S. Appl. No. 11/675,275, filed 2003.
U.S. Appl. No. 11/813,329, filed 2007.
U.S. Appl. No. 10/575,099, filed 2007.
English Language Abstract of JP 10-057477, (1998).
English Language Abstract of JP 11-012182, (1999).
English Language Abstract of JP 60-193468, (1985).
English Language Abstract of JP 1-224324, (1989).
English Language Abstract of JP 7-124255, (1995).
English Language Abstract of JP 2-203909, (1988).
English Language Abstract of WO 2004/050146, (2004).

\* cited by examiner

METHOD FOR REMOVING LEUKOCYTE AND FILTER FOR USE THEREIN

TECHNICAL FIELD

The present invention relates to a method for trapping leukocytes from leukocyte-containing liquids such as blood and to a leukocyte-removing filter for trapping leukocytes from leukocyte-containing solutions such as blood or for use in a leukocyte-removing treatment by extracorporeal circulation of blood.

BACKGROUND ART

In the field of transfusion, a whole-blood product, an erythrocyte product, a platelet product, a plasma product, and the like are used according to the need of recipients. In recent years, leukocyte-free blood transfusion in which a blood product is transfused after removing leukocytes contained in the blood product has been widely used. This is because it was found that relatively slight side effects accompanying blood transfusion, such as headache, nausea, chill, or febrile non-hemolytic reaction, or serious side effects which seriously affect a recipient, such as alloantigen sensitization, viral infection, or post-transfusion graft versus host disease (GVHD), are mainly caused by leukocytes contained in the blood product used for blood transfusion.

It is considered that relatively slight side effects such as headache, nausea, chill, and fever can be prevented by removing leukocytes in the blood product until the leukocyte residual rate becomes $10^{-1}$ to $10^{-2}$ or less. It is considered that leukocytes must be removed until the residual rate becomes $10^{-4}$ to $10^{-6}$ or less in order to prevent serious side effects such as alloantigen sensitization or viral infection.

In recent years, leukocyte-removing therapy using extracorporeal blood circulation has been conducted for treating diseases such as rheumatism or ulcerative colitis, and has achieved excellent clinical effects.

As a method for removing leukocytes from a blood product, a filter method of removing leukocytes using a filter material made from fiber mass such as nonwoven fabric or a porous structure with continuous pores has been most widely used due to advantages such as operational simplicity, low cost, and the like.

In the mechanism of leukocyte removal using the filter material such as fiber mass such as nonwoven fabric or a porous structure having continuous pores, it is considered that leukocytes coming into contact with the surface of the filter material adhere to or are adsorbed on the surface of the filter material. Therefore, as a means for improving the leukocyte-removing performance of the conventional filter material, a method of increasing the contact frequency between the filter material and leukocytes, specifically, studies of reducing the fiber diameter or the pore size of the nonwoven fabric or increasing the bulk density has been performed (see Patent Document 1). However, since the pressure drop is increased when causing the blood product to pass through the filter material accompanying improvement of the leukocyte-removing performance, there has been a problem that the filtration speed is significantly decreased before completing the filtration of a desired amount of blood.

On the other hand, as to the porous structure having continuous pores, a porous material having a bubble point of 0.08 to 0.3 kg/cm² is disclosed as a leukocyte separation material free from clogging with leukocytes (see Patent Document 2). However, the inventors of the present invention have examined and found that this leukocyte separation material is suitable for reducing leukocytes contained in the blood product to $10^{-2}$ to $10^{-3}$, and possesses the following problem when using a porous material having a relatively small average pore diameter necessary for achieving a leukocyte residual rate of $10^{-4}$ which is the target value of the present invention. Specifically, although a filter exhibiting high leukocyte-removing performance can be obtained by using a porous material with an appropriate average pore diameter, such a porous material has a high pressure drop due to clogging of leukocytes and the like at the same time, resulting in a significant decrease of the blood filtration speed in the same manner as in the case of using nonwoven fabric having a small fiber diameter.

In recent years, the medical treatment field has posed additional demands for the leukocyte-removing filter. One of the demands is improvement of the recovery rate of useful components in addition to improvement of the leukocyte-removing performance. Blood as the raw material for the blood product is mainly valuable blood provided by a goodwill blood donation. However, uncollectible blood remaining in the leukocyte-removing filter is disposed of together with the filter and frittered away. Therefore, it is extremely meaningful to improve the recovery rate of useful components in comparison with the existing leukocyte-removing filter.

Therefore, in order to satisfy the above-described demand from the medical treatment field, a leukocyte-removing filter with a smaller amount of packed filter material by using a leukocyte-removing filter material having a high leukocyte-removing performance per unit volume has been demanded. Use of such a filter reduces the amount of blood remaining in the filter due to a reduction in the amount of filter material packed and makes it unnecessary to perform the operation of collecting useful components remaining in the filter, whereby the recovery rate of useful components is expected to be increased in comparison with a conventional filter.

As another demand for the leukocyte-removing filter in the market, there is a demand for treating a desired amount of blood in a short period of time. In order to satisfy such a demand, the leukocyte-removing filter is expected to have such a shape that the cross-sectional area of the filter is equal to or greater than that used in a conventional filter and the thickness of the filter material is reduced. It is necessary to increase the leukocyte-removing performance per unit volume in order to reduce the thickness of the filter material while maintaining the leukocyte-removing performance.

In order to satisfy such demands, attempts to improve the leukocyte-removing performance per unit volume have been made by increasing uniformity of property elements of the filter material. As a material in which the property elements of the filter material are made uniform in the technical field aiming at removing leukocytes, a leukocyte trapping material in which the volume of the pore section useful for leukocyte removal is increased by narrowing the pore size distribution (see Patent Document 3), and a three-dimensional mesh-like continuous porous material having a uniform pore size in which the ratio of the volume average pore diameter to the number average pore diameter is 1.5 to 2.5 (see Patent Document 4) have been proposed. As nonwoven fabric as the filter material, nonwoven fabric in which uniformity of the fiber diameter is improved by narrowing the fiber diameter distribution has been proposed (see Patent Documents 5 and 6).

In addition, it is known that the effective utilization factor of the filter material is improved by using nonwoven fabric with a formation index of 15 to 50 corresponding to a thickness of 0.3 mm as a filter material, because if such a filter material is used, blood flows evenly in the thickness direction of a filter in the entire filter area (see Patent Document 7).

In this manner, attempts to increase the leukocyte-removing performance per unit volume have been made by making the pore size or the fiber diameter and properties in the thickness direction of the filtration surface of the filter material uniform. However, the above prior arts are only concerned about the properties in the direction in which the liquid flows (i.e. the direction vertical to the filtration surface). Specifically, the prior art documents do not take into account the importance of a liquid flow while diffusing three-dimensionally and uniformly within a filter material. Even if uniformity of the pore size and fiber diameter is controlled in an optimal range, there is a limitation to the operation of avoiding or inhibiting clogging and increase of pressure drop, while improving leukocyte-removing performance per unit volume.

Therefore, a leukocyte-removing method satisfying the conflicting demands of excellent flowability and high leukocyte-removing performance in medical treatment field at the same time and a leukocyte-removing filter possessing sufficient performance have been desired.

[Patent Document 1] JP-B-H02-13587
[Patent Document 2] JP-A-H01-224324
[Patent Document 3] WO 93/03740
[Patent Document 4] JP-A-H07-124255
[Patent Document 5] JP-A-S63-175157
[Patent Document 6] JP-2811707
[Patent Document 7] WO 2004/050146

DISCLOSURE OF THE INVENTION

Problems to be Solved by the Invention

In order to solve the above problems in the prior arts and satisfy the new demands from the medical treatment field, an object of the present invention is to provide, in the method of removing leukocytes using a leukocyte-removing filter, a method exhibiting a higher leukocyte-removing performance per unit volume of the filter and free from clogging and increasing the pressure drop. Another object of the present invention is to provide a leukocyte-removing filter used in the above method.

Means for Solving the Problems

The inventors of the present invention have conducted extensive studies concerning the case of treating a leukocyte-containing liquid, which tends to cause clogging due to high viscosity, using a leukocyte-removing filter, while paying attention to the importance that the liquid uniformly diffuses and flows within the filter material.

As a result, the inventors have found that a leukocyte-removing filter exhibiting a high leukocyte-removing performance per unit volume and free from clogging and remarkable increasing in pressure drop can be obtained by using a filter material in which ease of fluid flowability (permeation coefficient) in the direction vertical to the filtration surface and the direction parallel to the filtration surface is appropriately set, rather than by using a filter making only a single property element uniform as known in the prior art.

Specifically, the present invention includes the followings:

(1) A method for removing leukocytes from a leukocyte-containing liquid using a leukocyte-removing filter comprising a container having a liquid inlet and outlet and a porous filter material packed in the container, wherein the filter comprises a porous filter material having a permeation coefficient (kx) in the direction vertical to the filtration surface of $0.5 \times 10^{-12}$ m$^2$ to $2.0 \times 10^{-12}$ m$^2$ and a ratio (ky/kx) of a permeation coefficient (ky) in the direction parallel to the filtration surface to the permeation coefficient (kx) of 0.5 to 1.5.

(2) The method for removing leukocytes according to (1), wherein the permeation coefficient (kx) of the porous filter material is $1.0 \times 10^{-12}$ m$^2$ to $2.0 \times 10^{-12}$ m$^2$ and the permeation coefficient (ky) is $1.0 \times 10^{-12}$ m$^2$ m$^2$ to $3.0 \times 10^{-12}$ m$^2$.

(3) The method for removing leukocytes according to (1) or (2), wherein the porous filter material is a nonwoven fabric.

(4) A leukocyte-removing filter for removing leukocytes from a leukocyte-containing liquid comprising a container having an inlet and an outlet and a porous filter material packed in the container, wherein the filter comprises a porous filter material having a permeation coefficient (kx) in the direction vertical to the filtration surface of $0.5 \times 10^{-12}$ m$^2$ to $2.0 \times 10^{-12}$ m$^2$ and a ratio (ky/kx) of a permeation coefficient (ky) in the direction parallel to the filtration surface to the permeation coefficient (kx) of 0.5 to 1.5.

(5) The leukocyte-removing filter according to (4), wherein the permeation coefficient (kx) of the porous filter material is $1.0 \times 10^{-12}$ m$^2$ to $2.0 \times 10^{-12}$ m$^2$ and the permeation coefficient (ky) is $1.0 \times 10^{-12}$ m$^2$ to $3.0 \times 10^{-12}$ m$^2$.

(6) The leukocyte-removing filter according to (4) or (5), wherein the porous filter material is a nonwoven fabric.

Effects of the Invention

Since the leukocyte-removing method and the filter used for the method of the present invention exhibit high leukocyte-removing performance while inhibiting clogging and increasing the pressure drop, the method and the filter are very effective for trapping leukocytes contained in blood and blood products.

BEST MODE FOR CARRYING OUT THE INVENTION

The present invention will now be explained in detail.

The leukocyte-containing liquid used in the present invention refers to the generic name for a body fluid and synthetic blood containing leukocytes. In more detail, the leukocyte-containing liquid refers to whole blood and a single or multiple blood component-containing liquid prepared from whole blood, such as whole blood, red cell concentrate, washed red cell suspension, frozen-thawed concentrated red cells, synthetic blood, platelet poor plasma (PPP), platelet rich plasma (PRP), plasma, frozen plasma, platelet concentrate, and buffy coat (BC), a solution in which an anticoagulant, a preservative solution, or the like is added to the above-mentioned liquid, a whole blood product, a red cell product, a platelet product, a plasma product, and the like.

The permeation coefficient referred in the present invention is a constant showing ease of fluid flow used with Darcy's equation showing flow of a fluid in a porous material, and can be determined using the following equation (1).

$$k=(dt/dp) \times \mu \times v \quad (1)$$

wherein k is a permeation coefficient ($m^2$), dp is pressure drop (Pa), dt is thickness (m), $\mu$ is viscosity (Pa·s), and v is flow rate (m/s).

A large permeation coefficient indicates that the porous material has a structure in which a fluid easily flows; whereas a small permeation coefficient indicates that the porous material has a structure in which a fluid flows only with difficulty. Specifically, the equation (1) shows the relationship between the flow rate (v) and the pressure drop (dp) when a fluid having a viscosity ($\mu$) flows through a porous material with a thickness (dt). When this is transposed to Ohm's law concerning current and voltage, the pressure drop, flow rate and ($\mu \times dt$)/k correspond to the voltage, current and resistance, respectively. Since the resistance against a flow is expressed by the viscosity $\mu$ which is a property value of the fluid, the thickness dt of the porous material which is an apparent pass length, and the permeation coefficient k having a dimension of [$m^2$], the permeation coefficient may be considered to correspond to the cross-sectional area of the flow channel. On the other hand, since the permeation coefficient k is a value calculated using the equation (1) based on the result of measurement and the equation (1) uses the thickness dt of a porous material instead of the length of an actual complicated flow channel in the porous material, the permeation coefficient k, which is area information, also includes an effect of the true flow channel length partially. Therefore, a small permeation coefficient indicates a small cross-sectional area of a flow channel or a long flow channel length through which a fluid passes.

In the present invention, the permeation coefficient was measured as follows.

<Permeation Coefficient in the Direction Vertical to Filtration Surface (Hereinafter Referred to as "Vertical Permeation Coefficient")>

Figure 1:
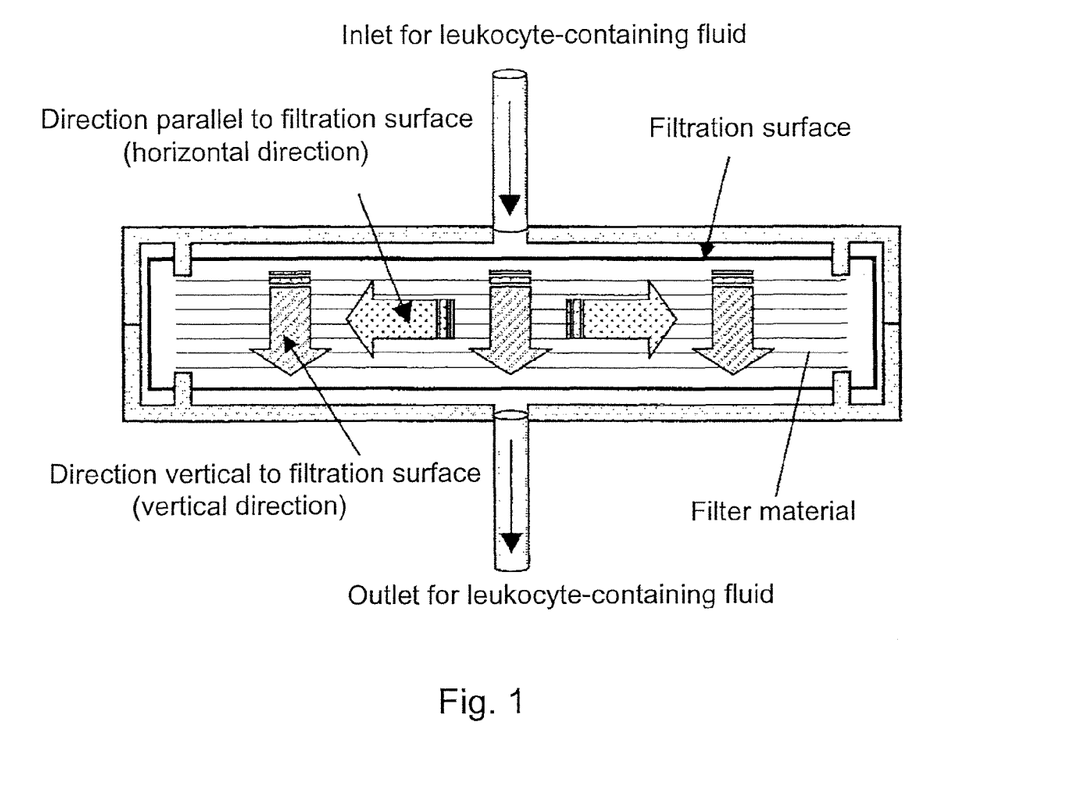
FIG. 1 is a schematic diagram showing the direction vertical to the filtration surface and the direction parallel to the filtration surface.

The vertical permeation coefficient in the present invention is a permeation coefficient obtained when a fluid is caused to flow from the direction vertical to a filtration surface. Here, the direction vertical to a filtration surface indicates the up/down direction (vertical direction) when a leukocyte-containing liquid is caused to flow from the inlet to the outlet as shown in FIG. 1, for example, whereas the direction parallel to the filtration surface indicates the left/right direction (horizontal direction). The air-flow pressure drop dpx of the vertical direction was determined by measuring the pressure difference with the atmosphere, when air was caused to flow at a flow rate of 0.1 l/min in a column with an opening diameter of 1.3 cm and packed with a filter material prepared to the thickness of about 1.0 mm. In order to ensure a fluid flow, open spaces of 1 mm or more were provided on the inlet side and the outlet side of the filter material in the column. The vertical permeation coefficient (kx) was calculated by substituting the resulting value of pressure drop, the filter material thickness as dtx, viscosity of air as $\mu$x, and the flow rate of air as vx to the equation (1). The thickness of the filter material was determined by measuring the thickness of the center using a thickness meter (Ozaki Mfg. Co., Ltd., PEACOCK Model G).

<Permeation Coefficient in the Direction Parallel to the Filtration Surface (Hereinafter Referred to as "Horizontal Permeation Coefficient")>

Figure 2:
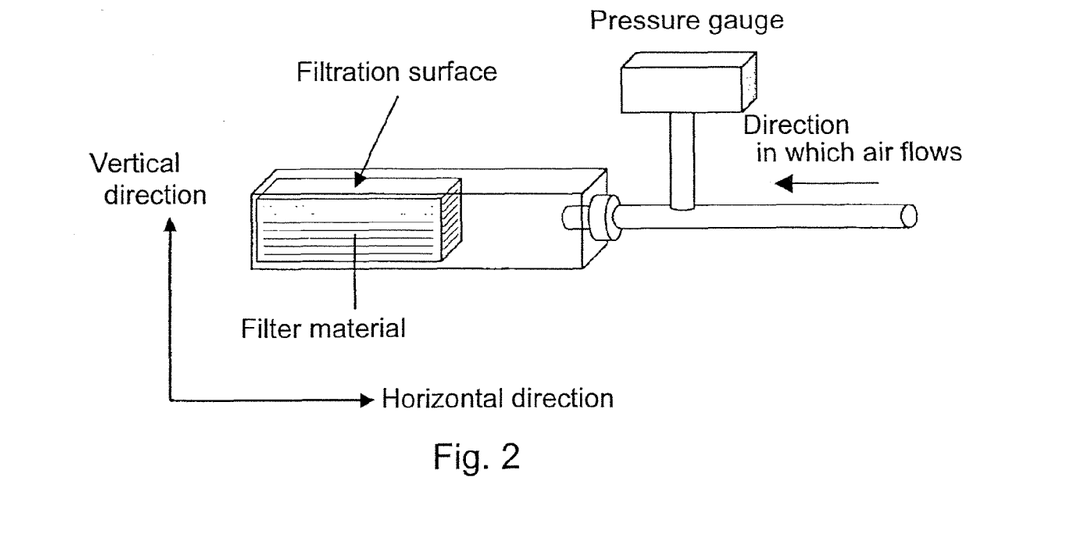
FIG. 2 is a schematic diagram showing a method of packing the filter material when measuring a horizontal permeation coefficient.

For measuring the air-flow pressure drop dpy in the horizontal direction, a filter material was formed into a 0.9 cm×0.9 cm×2 cm rectangular parallelepiped (filtration surface size: 0.9 cm×2 cm) and packed in a rectangular parallelepiped container with a 1.0 cm×1.0 cm outlet and a length of 4 cm, as shown in FIG. 2. When the thickness of the filter material is smaller than 0.9 cm, it is preferable to stack an additional amount of filter material to a thickness of 0.9 cm. If the thickness is greater than 0.9 cm, a portion of the filter material is preferably peeled off or removed by grinding to reduce the thickness to 0.9 cm. The pressure difference between the atmosphere and the inside of the rectangular parallelepiped container was measured when air was caused to flow through the filter material packed in the container at a flow rate of 0.1 l/min. In this instance, filler which does not penetrate into the filter material was filled between the filter material and the rectangular parallelepiped container in order to prevent air leakage. The horizontal permeation coefficient (ky) was calculated by substituting the resulting value of pressure drop, 2 cm as dty, viscosity of air as By, and the flow rate of air as vy, to the equation (1).

The vertical permeation coefficient (kx) of the filter material used in the present invention must be $0.5 \times 10^{-12}$ $m^2$ or more, but not more than $2.0 \times 10^{-12}$ $m^2$. If the vertical permeation coefficient (kx) is less than $0.5 \times 10^{-12}$ $m^2$, the permeation resistance of leukocyte-containing liquid increases, resulting in unpreferable clogging and retardation of filtration. If the vertical permeation coefficient (kx) exceeds $2.0 \times 10^{-12}$ $m^2$, on the other hand, the resistance decreases when the leukocyte-containing liquid flows through the filter material, that is it indicates that the cross-sectional area of the flow channel is large or the length of the flow channel is short. As a result, unpreferably, leukocytes cannot be sufficiently trapped. The value of the vertical permeation coefficient (kx) is more preferably $0.7 \times 10^{-12}$ $m^2$ to $2.0 \times 10^{-12}$ $m^2$, still more preferably $1.0 \times 10^{-12}$ $m^2$ to $2.0 \times 10^{-12}$ $m^2$, and particularly preferably $1.2 \times 10^{-12}$ $m^2$ to $2.0 \times 10^{-12}$ $m^2$.

In addition, the ratio (ky/kx) of the horizontal permeation coefficient (ky) to the vertical permeation coefficient (kx) of the filter material used in the present invention must be 0.5 to 1.5. The ratio (ky/kx) in this range reduces the anisotropy of a flow and ensures a diffusive manner of flow similar to heat conduction, whereby the fluid can flow without being significantly interfered with by occurrence of flow inhibiting points such as clogging. An excellently balanced filter ensuring both excellent flowability and high leukocyte-removing performance can be obtained by appropriately controlling the balance between the flowability in the direction vertical to the filtration surface and the flowability in the direction parallel to the filtration surface. Specifically, notwithstanding possessing the filtration resistance sufficient to trap leukocytes, excellent flowability is ensured even when flow is inhibited in some pores in the porous material, because the liquid can move to other pores. Therefore, the effect that the above contradictory characteristics can be maintained at the same time may be obtained. If the ratio (ky/kx) is less than 0.5, a liquid flows with difficulty in the direction horizontal to the filtration surface as compared with the direction vertical to the filtration surface. Therefore, if some pores in the filter material are clogged, blood can move to the other pores only with difficulty, resulting in an increase of the resistance against the blood flow. Moreover, clogging increases due to blood continuing to flow to the clogged area, whereby filtration is retarded. If the ratio (ky/kx) is more than 1.5, on the other hand, since a liquid easily flows in the direction horizontal to the filtration surface as compared with the direction vertical to the filtration surface, filtration is retarded due to an increase in the flow channel length including the bypass of the clogged areas, and clogging and pressure drop increase easily occur. If the ratio (ky/kx) is 0.5 to 1.5, a flow parallel to the filtration surface can be ensured. The filtration time can be reduced, because the liquid can efficiently move to the other pores, even if some pores interfere with flow of a fluid. More preferably the ratio (ky/kx) is 0.7 to 1.5, still more preferably 1.0 to 1.5.

In order to obtain a filter material excellent in the balance of better flow properties and high leukocyte-removing performance, the horizontal permeation coefficient (ky) is preferably $0.5 \times 10^{-12}$ m$^2$ to $3.0 \times 10^{-12}$ m$^2$, more preferably $1.0 \times 10^{-12}$ m$^2$ to $3.0 \times 10^{-2}$ m$^2$, still more preferably $1.2 \times 10^{-12}$ m$^2$ to $3.0 \times 10^{-12}$ m$^2$, and particularly preferably $1.5 \times 10^{-12}$ m$^2$ to $3.0 \times 10^{-12}$ m$^2$.

Figure 4:
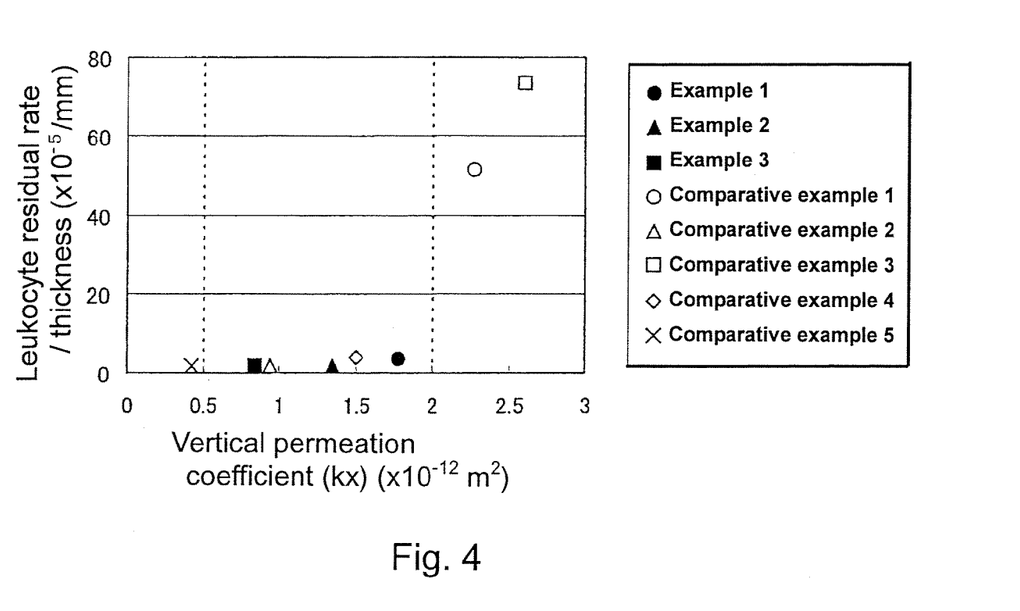
FIG. 4 is a graph showing the relationship between the vertical permeation coefficient and the ratio of the leukocyte residual rate to the thickness of the filter materials used in the leukocyte-removing filters of Examples 1 to 3 and Comparative examples 1 to 5.
Figure 5:
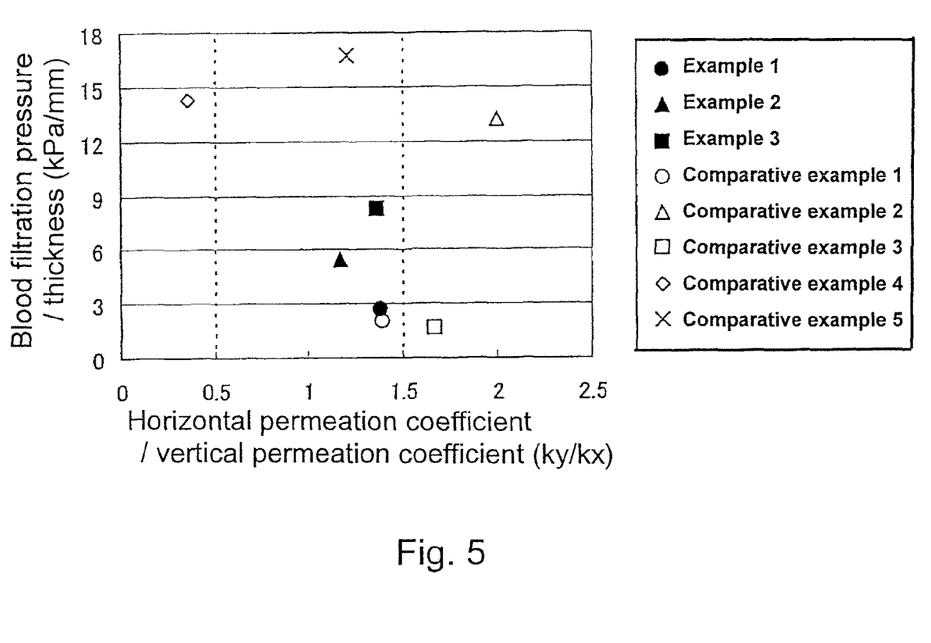
FIG. 5 is a graph showing the relationship between the vertical permeation coefficient and the ratio of the blood filtration pressure to the thickness of the filter materials used in the leukocyte-removing filters of Examples 1 to 3 and Comparative examples 1 to 5.

The significance of the range of the permeation coefficient values described above is clear from FIG. 4 and FIG. 5 showing the results obtained in Examples 1 to 3 and Comparative examples 1 to 5. It can be seen from these Figures that when the vertical permeation coefficient is greater than $2.0 \times 10^{-12}$ m$^2$ (Comparative examples 1 and 3), high leukocyte-removing performance cannot be obtained. It can be also understood that even if high leukocyte-removing performance is be obtained, flowability is not excellent in the case in which the ratio of the horizontal permeation coefficient to the vertical permeation coefficient is smaller than 0.5 (Comparative example 4) or greater than 1.5 (Comparative example 2), or the vertical permeation coefficient is smaller than 0.5 (Comparative example 5), because the ratio of blood filtration pressure to the thickness increases in these cases. Therefore, a filter material having high leukocyte-removing performance and excelling in flowability can be obtained by maintaining the vertical permeation coefficient of $0.5 \times 10^{-12}$ m$^2$ to $2.0 \times 10^{-12}$ m$^2$ and the ratio of the horizontal permeation coefficient to the vertical permeation coefficient of 0.5 to 1.5.

The permeation coefficient is a parameter determined by various factors such as a fiber diameter, filling rate, orientation of fibers, dispersibility of fibers, and the like in the case in which the filter material is nonwoven fabric, for example. Therefore, the permeation coefficient varies depending on these factors. Because these factors affect both the vertical permeation coefficient and the horizontal permeation coefficient, if one of the permeation coefficients increases, the other permeation coefficient may increase or decrease. Therefore, in order to obtain a filter material having a vertical permeation coefficient and a ratio of the horizontal permeation coefficient to vertical permeation coefficient within the range of the present invention, the relationship between the properties of a selected filter material and the vertical permeation coefficient or the horizontal permeation coefficient must be clarified and these factors must be comprehensively selected and controlled. For example, if a factor having a small effect on one of the vertical permeation coefficient and the horizontal permeation coefficient is selected and controlled, it is possible to control each permeation coefficient, and a filter material with optimal permeation coefficients can be obtained. It is difficult to determine the relationship between the selected factors and the permeation coefficients, because this differs depending on kinds of filter material used. When the filter material is nonwoven fabric, for example, one method of controlling the permeation coefficients can be shown as follows. It can be confirmed by experiment that the vertical permeation coefficient changes by a factor of 0.3 and the horizontal permeation coefficient changes by a factor of 0.5 by increasing the filling rate by a factor of 1.7, provided the fiber diameter is the same. Therefore, the ratio of the horizontal permeation coefficient to the vertical permeation coefficient can be controlled by controlling the filling rate. In addition, it can be confirmed by experiments that the vertical permeation coefficient increases by a factor of 1.6, with the horizontal permeation coefficient remaining the same by increasing the fiber diameter by a factor of 2, provided the filling rate is the same. Therefore, only the vertical permeation coefficient can be controlled by controlling the fiber diameter. In addition, because it can be confirmed that the vertical permeation coefficient decreases and the horizontal permeation coefficient increases by changing the orientation of fibers in the thickness direction and the vertical permeation coefficient decreases more significantly than the horizontal permeation coefficient by improving fiber dispersibility, the ratio of the horizontal permeation coefficient and the vertical permeation coefficient can be controlled. However, it is difficult in many cases to obtain a filter material satisfying the requirements of the present invention by controlling a single factor. A comprehensive control of various factors is necessary.

Figure 3:
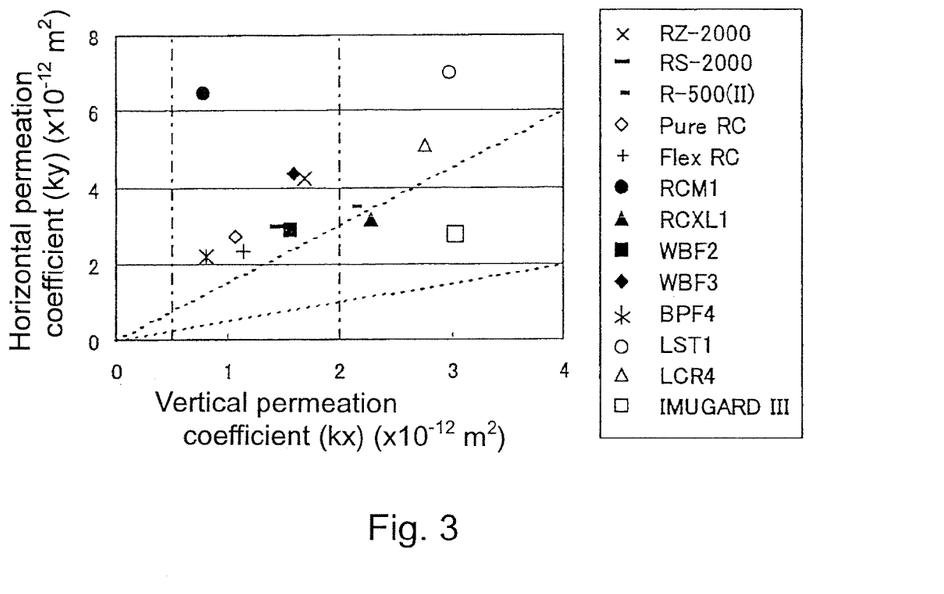
FIG. 3 is a graph showing the relationship between the vertical permeation coefficient and the horizontal permeation coefficient of the filter material used in a conventional leukocyte-removing filter.

Note that the inventors of the present invention have measured the vertical permeation coefficient and horizontal permeation coefficient of filter materials used in conventional leukocyte-removing filters according to the above-described method, but found no leukocyte-removing filters using a filter material with the permeation coefficient satisfying the requirements of the present invention (FIG. 3).

The leukocyte-removing filter of the present invention comprises a container having a liquid inlet and outlet and a filter material packed in the container. The filter may be formed from a single filter material or a plurality of filter materials. In the case in which the filter is formed from a plurality of filter materials, it is sufficient for the filter to contain at least one filter material satisfying the previously-described requirements of the permeation coefficient (kx) and the ratio of (ky/kx). Of course, a combination of two or more such filter materials is acceptable. A configuration in which a first filter material for removing micro aggregates is disposed on the upstream side and a second filter material for removing leukocytes is disposed downstream of the first filter material is preferable. For example, a filter material comprising nonwoven fabric having a fiber diameter of several to several tens of μm may be disposed on the inlet side as the first filter material for removing aggregates, a filter material comprising nonwoven fabric having a fiber diameter of 0.3 to 3.0 μm may be disposed as the second filter material for removing leukocytes, and, as required, a post filter material may be disposed downstream of the second filter material. In this case, the first filter material and the post filter material, of which the main purpose is not removal of leukocytes, need not necessarily satisfy the requirements of the permeation coefficient (kx) and the ratio (ky/kx), but the second filter material must satisfy these requirements. Either an arrangement of alternately disposing nonwoven fabric with a large fiber diameter and nonwoven fabric having a small fiber diameter, or an arrangement disposing nonwoven fabric with a large fiber diameter on the upstream side and nonwoven fabric with a smaller fiber diameter on the downstream side can be used. The latter arrangement is preferred.

In the case of a leukocyte-removing filter comprising a planar-shaped and flexible container, provision of the post filter material preferably prevents the filter material from being pressed against the container on the outlet side due to positive pressure on the inlet side during filtration, and prevents the container on the outlet side from adhering to the filter material due to negative pressure on the outlet side to hinder the blood flow. Moreover, weldability between the flexible container and the filter material is increased. As the post filter material, a conventional filter medium such as a fibrous porous medium such as a nonwoven fabric, woven fabric, or mesh, or a porous material having three-dimensional mesh-like continuous pores may be used. As the material for the post filter, polypropylene, polyethylene, styrene-isobutylene-styrene copolymer, polyurethane, polyester, and the like can be given. It is preferable that the post filter material be formed of nonwoven fabric from the viewpoint of productivity and weld strength of the leukocyte-removing filter. It is particularly preferable that the post filter material have a plurality of protrusions formed by embossing or the like since the blood flow becomes more uniform. As a means for preventing blood flow inhibition, a method of preventing adhesion of a filter material to the container on the outlet side by providing concavities and convexities by molding projections on the inner surface of the flexible container, or by molding the flexible container itself in a furrow shape or a shape having concavities and convexities is effective.

As the material for the container in which the filter material is placed, a hard resin or a flexible resin may be used. As examples of the hard resin, a phenol resin, acrylic resin, epoxy resin, formaldehyde resin, urea resin, silicon resin, ABS resin, nylon, polyurethane, polycarbonate, polyvinyl chloride, polyethylene, polypropylene, polyester, styrene-butadiene copolymer, and the like can be given. In the case of using the flexible resin, the container is preferably formed of a sheet-like or cylindrical formed product of a flexible synthetic resin. The material for the container preferably has thermal and electrical properties similar to those of the material for the filter element. For example, soft polyvinyl chloride, polyurethane, ethylene-vinyl acetate copolymer, polyolefin such as polyethylene and polypropylene, thermoplastic elastomer such as hydrogenated styrene-butadiene-styrene copolymer, styrene-isoprene-styrene copolymer, or hydrogenated styrene-isoprene-styrene copolymer, a mixture of the thermoplastic elastomer, and softening agent such as polyolefin, ethylene-ethyl acrylate, or the like can be given as suitable materials. Of these, soft polyvinyl chloride, polyurethane, ethylene-vinyl acetate copolymer, polyolefin, and thermoplastic elastomers containing these polymers as a major component are preferable, with soft polyvinyl chloride and polyolefin being particularly preferable.

The shape of the container is not particularly limited insofar as the container has an inlet for a leukocyte-containing liquid and an outlet for a leukocyte-free liquid. It is preferable that the container has a shape conforming to the shape of the leukocyte removal filter material. In the case where the leukocyte removal filter material is in the shape of a planar plate, the shape of the container may be polygonal such as a tetragon or hexagon or a flat shape formed by a curve such as circular or elliptical. In more detail, it is preferable that the container include an inlet-side container having a liquid inlet and an outlet-side container having a liquid outlet, and the inlet-side container and the outlet-side container sandwich the leukocyte removal filter material directly or through a support to divide the inside of the filter into two compartments to form a flat leukocyte-removing filter. As another example, in the case where the leukocyte removal filter material is cylindrical, it is preferable that the container also be cylindrical. In more detail, it is preferable that the container includes a cylindrical body in which the filter material is placed, an inlet-side header including a liquid inlet, and an outlet-side header including a liquid outlet. The container is divided into two compartments by potting so that liquid introduced from the inlet flows from the outer circumferential side of the cylindrical filter to the inner circumferential side (or, from the inner circumferential side to the outer circumferential side) to form a cylindrical leukocyte-removing filter.

The porous filter material used in the present invention refers to fiber mass such as a nonwoven fabric manufactured by a melt-blow method, a flash spinning method, a papermaking method, or the like or a filter material formed from a porous material having continuous pores such as a sponge structure having continuous pores. Among the porous materials, nonwoven fabric is most preferable from the viewpoint of ease of manufacturing, ease of handling and processing, and the like. As the raw material for the porous material, polyvinyl formal, polyurethane, poly(meth)acrylate, polyacrylonitrile, polyvinyl acetal, polyester, polyamide, polysulfone, polystyrene, polyethylene, polypropylene, cellulose, cellulose acetate, hemp, cotton, silk, glass, carbon, and the like are suitable.

The shape of the filter material is not particularly limited. For example, a material obtained by layering sheets of the filter material in the shape of a planar plate, and a material obtained by cylindrically forming the planar-plate-shaped material can be given. The former material has been widely used for a blood transfusion filter or the like, since it is compact and can be relatively easily formed. Since the latter material is suitable for the treatment of a large quantity of liquid, that material is preferably used as a filter for extracorporeal circulation.

In order to control the selective separation properties of blood cell and surface hydrophilicity, the surface of the filter material may be modified by using a known technology such as coating, chemical treatment, or radiation treatment.

The filling rate of the porous material is preferably 0.05 to 0.30, still more preferably 0.07 to 0.25, and particularly preferably 0.07 to 0.20. If the filling rate is greater than 0.30, the flow resistance of the porous material is increased, whereby flowability is unpreferably decreased. If the filling rate is less than 0.05, leukocytes pass through the porous material without being trapped by the porous material, whereby the leukocyte-removing performance is decreased. Moreover, unpreferably, mechanical strength of the porous material is also decreased.

The filling rate of the porous material used in the present invention is determined by measuring the area, thickness, and weight of the porous material cut to arbitrary dimensions and the specific gravity of the material which makes up the porous material, and calculating using the following equation (2). The thickness was measured using a thickness meter (Ozaki Mfg. Co., Ltd. Peacock Model G).

$$\text{Filling rate} = \{\text{weight of porous material (g)}/(\text{area of porous material (cm}^2) \times \text{thickness of porous material (cm)})\}/\text{specific gravity of material making up porous material (g/cm}^3) \qquad (2)$$

The average pore diameter of the porous material is preferably 1 μm to 10 μm, more preferably 2 μm to 8 μm, and still more preferably 2 μm to 6 μm. If the average pore diameter is less than 1 μm, the porous material becomes clogged with blood components, resulting in a decrease in flowability; if the average pore diameter is more than 10 μm, the probability of leukocytes passing through the porous material increases. The average pore diameter in the present invention is measured using Automated Perm Porometer (Porous Materials, Inc., U.S.) in a sample chamber with a sample size of 4.25 cm, after dipping a porous material having one edge of about 5 cm and a thickness of about 0.6 mm in a fluorine-containing inert liquid "FC-43" (Mitsubishi 3M, Inc.).

When the porous material is made from a fiber mass such as nonwoven fabric, the average fiber diameter of the nonwoven fabric is 0.3 to 3.0 μm, preferably 0.5 to 2.7 μm, still more preferably 0.5 to 2.5 μm, and particularly preferably 0.8 to 2.5 μm. If the average fiber diameter is greater than 3.0 μm, occurrence of contact with leukocytes is reduced due to a decrease in the specific surface area, whereby it trends to become difficult to trap leukocytes. If the average fiber diameter is less than 0.3 μm, clogging caused by blood cells tends to be increased.

The average fiber diameter here refers to a value determined according to the following procedure. Specifically, portions of the filter material considered to be substantially uniform are sampled at several points from one sheet of nonwoven fabric or a plurality of sheets of nonwoven fabric having substantially same quality making up the filter material, and photographed using a scanning electron microscope or the like. The filter material is continuously photographed until the total number of fibers photographed exceeds 100, and the diameters of all the fibers appearing in the photographs thereby obtained are measured. The diameter used herein refers to the width of the fiber in the direction perpendicular to the fiber axis. A value obtained by dividing the sum of the diameters of all the fibers measured by the number of fibers is defined as the average fiber diameter. However, when plural fibers are overlapped each other, and a fiber is hidden behind another fiber, whereby the width cannot be measured, when fibers are melted to form a thick fiber, when fibers with a diameter significantly differing from each other are mixed, when the boundary of the fiber is not clear due to incorrect focusing, or the like, the data obtained is eliminated. If the average fiber diameter significantly differs between the upstream side and the downstream side, such a material is not regarded to be a single filter material. The term "the average fiber diameter significantly differs" used herein refers to the case where a significant difference is statistically recognized. In this case, the upstream side and the downstream side of the material are considered to be different filter materials, and the average fiber diameters of the upstream side and the downstream side are separately measured after identifying the interface between the upstream side and the downstream side.

In the present invention, the formation index was measured using a formation tester FMT-MIII (Nomura Shoji Co., Ltd.; manufactured in 2002; S/N: 130). The basic setting was not changed after shipment from the factory, and the measurement was carried out at about 3400 of the total number of pixels using a CCD camera. In the present invention, the formation index was measured while adjusting the measurement size to 7 cm×3 cm (one pixel size=0.78 mm×0.78 mm) so that the total number of pixels was about 3,400. However, the measurement size may be changed corresponding to the shape of the sample so that the total number of pixels is equal. Since the formation index is significantly affected by the thickness of the nonwoven fabric, the formation index corresponding to a thickness of 0.3 mm was calculated using the following method. Specifically, three sheets of nonwoven fabric having substantially same quality and a uniform thickness of 0.3 mm or less are provided, and the formation index and the thickness of each sheet are measured. The thickness is measured at four points using a thickness meter (Ozaki Mfg. Co., Ltd., PEACOCK Model G), and the average value is defined as the thickness of the nonwoven fabric. Then, two of the three sheets of the nonwoven fabric are placed one upon another so that the thickness is 0.3 mm or more, and the formation index and the thickness are measured. After completing the formation index measurement for all three combinations, a linear regression equation of the thickness and the formation index is created, and the formation index at a thickness of 0.3 mm is calculated using the equation. In the case where the total thickness of two sheets of the nonwoven fabric does not reach 0.3 mm, sheets of nonwoven fabric are placed one upon another so that the thickness is 0.3 mm, and the formation index is measured. The number of sheets of nonwoven fabric is then reduced so that the thickness is 0.3 mm or less, and the formation index is measured. The formation indices are measured for all nonwoven fabric combinations in which the total thickness is 0.3 mm or less. Then, a linear regression equation of the thickness and the formation index was created, and the formation index at a thickness of 0.3 mm is calculated using the equation. The nonwoven fabric having substantially same quality means that the properties of the nonwoven fabric (material, fiber diameter, filling rate, and the like) are identical. In the case where sheets of nonwoven fabric having substantially same quality necessary for measurement cannot be obtained from a single filter, the formation index may be measured by combining sheets of nonwoven fabric of the same type of filter.

The nonwoven fabric used in the present invention can be manufactured by using either a wet method or a dry method. In particular, the nonwoven fabric is preferably manufactured by using a melt-blow method, a flash spinning method, or a papermaking method, since an ultrafine fiber can be obtained.

An example of the melt-blow method is described below as the manufacturing method for the nonwoven fabric in the present invention.

A molten polymer fluid melted in an extruder is filtered through an appropriate filter, introduced into a molten polymer inlet section of a melt-blow die, and discharged from an orifice nozzle. At the same time, a heated gas introduced into a heated gas inlet section is introduced into a heated gas discharge slit formed by the melt-blow die and a lip. The molten polymer discharged is attenuated by discharging the heated gas from the slit to cause ultrafine fibers to be formed, and stacked to obtain nonwoven fabric. In this instance, nonwoven fabric with a desired fiber diameter and weight per square meter (metsuke) can be obtained and the fiber orientation and dispersibility of the fiber can be controlled by appropriately selecting and controlling various spinning factors such as resin viscosity, melting temperature, discharge amount per single pore, heating gas temperature, heating gas pressure, distance between spinneret and accumulation net, and the like, according to the types of resin. Furthermore, it is possible to control the thickness of the nonwoven fabric, i.e., the filling rate, by hot press processing.

As the raw material for the nonwoven fabric, polyester, polyamide, polyacrylonitrile, polypropylene, and the like are preferable, with particularly preferable materials being polyethylene terephthalate, polybuthylene terephthalate, and polypropylene.

The leukocyte-removing method of the present invention will be described below. However, the present invention is not limited to the following description.

In the leukocyte-removing method, leukocytes may be removed by allowing a leukocyte-containing liquid to flow into the leukocyte-removing filter from a container containing the leukocyte-containing liquid provided at a position higher than the leukocyte-removing filter through a tube by utilizing head drop, or leukocytes may be removed by allowing a leukocyte-containing liquid to flow by increasing pressure to the leukocyte-containing liquid from the inlet side of the leukocyte-removing filter and/or decompressing the leukocyte-containing liquid from the outlet side of the leukocyte-removing filter using a means such as a pump.

Any method of preparing leukocyte-free blood products using a filter may be used without specific limitations.

A leukocyte-removing method using the leukocyte-removing filter in extracorporeal circulation therapy is described below.

After priming the inside of the leukocyte-removing filter using a physiological saline solution or the like, the liquid inside the leukocyte-removing filter is replaced with a solution containing at least an anticoagulant such as heparin, nafamostat mesilate, ACD-A, or ACD-B. Blood is caused to flow into the inlet of the leukocyte-removing filter from a circuit connected with a human at a flow rate 10 to 200 ml/min while adding an anticoagulant to the blood which is caused to flow from the body to remove leukocytes using the leukocyte-removing filter. In the leukocyte-removing start period (throughput: 0 to 0.5 l), the flow rate is preferably 10 to 50 ml/min, and still more preferably 10 to 40 ml/min, and particularly preferably 10 to 30 ml/min. In the period after the leukocyte-removing start period (throughput: 0.2 to 12 l), the flow rate is preferably 20 to 120 ml/min, still more preferably 20 to 100 ml/min, and particularly preferably 20 to 60 ml/min. It is preferable to replace the liquid inside the leukocyte-removing filter with a physiological saline solution or the like after removing leukocytes to return the blood, since the blood inside the leukocyte-removing filter is not wasted.

The present invention is described below based on examples. However, the present invention is not limited to the following examples.

EXAMPLE 1

Nonwoven fabric formed of polyethylene terephthalate (hereinafter abbreviated as "PET") and having a thickness of 0.22 mm, a weight per square meter (metsuke) of 40 g/m$^2$, a filling rate of 0.14, an average fiber diameter of 1.4 μm, a formation index of 55, a vertical permeation coefficient of $1.78 \times 10^{-12}$ m$^2$, and a horizontal permeation coefficient of $2.46 \times 10^{-12}$ m$^2$ was used as a filter material. The vertical permeation coefficient and the horizontal permeation coefficient were measured by the above-mentioned method.

Next, the method for evaluating the leukocyte-removing performance and flowability of the filter material will be described. Blood used for evaluation was whole blood prepared by adding 14 ml of a CPD solution as an anticoagulant to 100 ml of blood immediately after collection, stirring the resulting mixture, and allowing the mixture to stand for two hours (hereinafter called "pre-filtration blood"). A column with an effective filtration area of 1.3 cm$^2$ was packed with eight sheets of nonwoven fabric. A syringe filled with the pre-filtration blood was connected with the inlet of the column through a polyvinyl chloride tube having an inner diameter of 3 mm and an outer diameter of 4.2 mm. The blood was caused to flow through the column at a flow rate of 1.2 ml/min using a syringe pump to collect 3 ml of the blood (hereinafter called "post-filtration blood"). The leukocyte-removing performance was evaluated by calculating the leukocyte residual rate. The leukocyte residual rate was determined by measuring the number of leukocytes using a flow cytometry method (apparatus: "FACS Calibur" manufactured by Becton, Dickinson and Company) and calculating the leukocyte residual rate according to the following equation (3).

Leukocyte residual rate=[leukocyte concentration (number of leukocytes per μl)(post-filtration blood)]÷[leukocyte concentration (number of leukocytes per μl)(pre-filtration blood)]     (3)

The number of leukocytes was measured by sampling 100 μl of each blood and using a "Leucocount" kit with beads (Nippon Becton Dickinson Co., Ltd.). The flowability was evaluated by measuring the blood filtration pressure. The blood filtration pressure was measured at the time of completion of filtration by connecting a pressure gauge to the tube on the input side of the column. As a result, the leukocyte residual rate/thickness was found to be $3.3 \times 10^{-5}$/mm and the blood filtration pressure/thickness was found to be 2.7 kPa/mm, configuring that the leukocyte-removing performance can be increased without increasing filtration pressure. The blood evaluation results of Examples 1 to 3 and Comparative examples 1 to 5 are summarized in FIG. 4 and FIG. 5. The dashed lines in FIG. 4 indicate lines for kx=$0.5 \times 10^{-12}$ m$^2$ and kx=$2.0 \times 10^{-12}$ m$^2$. The dashed lines in FIG. 5 indicate lines for ky/kx=0.5 and ky/kx=1.5.

EXAMPLE 2

Nonwoven fabric formed of PET and having a weight per square meter of 40 g/m$^2$, a thickness of 0.19 mm, a filling rate of 0.16, an average fiber diameter of 1.4 μm, a vertical permeation coefficient of $1.35 \times 10^{-12}$ m$^2$, a formation index of 53, and a horizontal permeation coefficient of $1.59 \times 10^{-12}$ m$^2$ was used as a filter material. The evaluation was conducted in the same manner as in Example 1. As a result, the leukocyte residual rate/thickness was $1.8 \times 10^{-5}$/mm and the blood filtration pressure/thickness was 5.4 kPa/mm.

EXAMPLE 3

Nonwoven fabric formed of PET and having a weight per square meter of 40 g/m$^2$, a thickness of 0.22 mm, a filling rate of 0.14, an average fiber diameter of 0.9 μm, a vertical permeation coefficient of $0.85 \times 10^{-12}$ m$^2$, a formation index of 61, and a horizontal permeation coefficient of $1.16 \times 10^{-2}$ m$^2$ was used as a filter material. The evaluation was conducted in the same manner as in Example 1. As a result, the leukocyte residual rate/thickness was $1.6 \times 10^{-5}$/mm and the blood filtration pressure/thickness was 8.3 kPa/mm.

COMPARATIVE EXAMPLE 1

Nonwoven fabric formed of PET and having a weight per square meter of 41 g/m$^2$, a thickness of 0.23 mm, a filling rate of 0.13, an average fiber diameter of 1.6 μm, a formation index of 65, a vertical permeation coefficient of $2.27 \times 10^{-2}$ m$^2$, and a horizontal permeation coefficient of $3.16 \times 10^{-12}$ m$^2$ was used as a filter material. The evaluation was conducted in the same manner as in Example 1. As a result, the leukocyte residual rate/thickness was $51.6 \times 10^{-5}$/mm and the blood filtration pressure/thickness was 2.0 kPa/mm. In this example, the filter had the permeation coefficient (kx) of greater than 2.0 and could not exhibit sufficient leukocyte-removing performance.

COMPARATIVE EXAMPLE 2

Nonwoven fabric formed of PET and having a weight per square meter of 41 g/m$^2$, a thickness of 0.18 mm, a filling rate of 0.17, an average fiber diameter of 1.1 μm, a formation index of 61, a vertical permeation coefficient of $0.95 \times 10^{-2}$ m$^2$, and a horizontal permeation coefficient of $2.00 \times 10^{-12}$ m$^2$ was used as a filter material. The evaluation was conducted in the same manner as in Example 1. As a result, the leukocyte residual rate/thickness was $1.7 \times 10^{-5}$/mm and the blood filtration pressure/thickness was 13.3 kPa/mm. In this example, the filter had a ky/kx value of greater than 1.5 and a high leukocyte-removing performance, but increased filtration pressure was observed.

COMPARATIVE EXAMPLE 3

Nonwoven fabric formed of PET and having a weight per square meter of 40 g/m², a thickness of 0.24 mm, a filling rate of 0.12, an average fiber diameter of 1.7 μm, a formation index of 59, a vertical permeation coefficient of $2.60 \times 10^{-12}$ m², and a horizontal permeation coefficient of $4.33 \times 10^{-12}$ m² was used as a filter material. The evaluation was conducted in the same manner as in Example 1. As a result, the leukocyte residual rate/thickness was $73.6 \times 10^{-5}$/mm and the blood filtration pressure/thickness was 1.7 kPa/mm. In this example, a greater number of leukocytes than in Comparative example 2 was passed through without being trapped due to the kx value greater than 2 and ky/kx value greater than 1.5. The filter thus could not exhibit sufficient leukocyte-removing performance.

COMPARATIVE EXAMPLE 4

Nonwoven fabric formed of PET and having a weight per square meter of 40 g/m², a thickness of 0.14 mm, a filling rate of 0.22, an average fiber diameter of 2.4 μm, a formation index of 62, a vertical permeation coefficient of $1.50 \times 10^{-12}$ m², and a horizontal permeation coefficient of $0.53 \times 10^{-12}$ m² was used as a filter material. The evaluation was conducted in the same manner as in Example 1. As a result, the leukocyte residual rate/thickness was $3.7 \times 10^{-5}$/mm and the blood filtration pressure/thickness was 14.3 kPa/mm. In this example, the filter had a ky/kx of smaller than 0.5 and thus a high leukocyte-removing performance, but increased filtration pressure was observed.

COMPARATIVE EXAMPLE 5

Nonwoven fabric formed of PET and having a weight per square meter of 41 g/m², a thickness of 0.15 mm, a filling rate of 0.22, an average fiber diameter of 1.6 μm, a formation index of 56, a vertical permeation coefficient of $0.43 \times 10^{-12}$ m², and a horizontal permeation coefficient of $0.52 \times 10^{-12}$ m² was used as a filter material. The evaluation was conducted in the same manner as in Example 1. As a result, the leukocyte residual rate/thickness was $1.8 \times 10^{-5}$/mm and the blood filtration pressure/thickness was 16.7 kPa/mm. In this example, the filter had a kx of smaller than 0.5 and thus a high leukocyte-removing performance, but increased filtration pressure was observed.

COMPARATIVE EXAMPLE 6

The vertical permeation coefficient and horizontal permeation coefficient of commercially available leukocyte-removing filters were measured according to the method described above. The brand names of commercially available filters evaluated were as follows: RZ-2000, RS-2000, R-500(II), Pure RC, and Flex RC manufactured by Asahi Kasei Medical Co., Ltd.; RCM1, RCXL1, WBF2, WBF3, and BPF4 manufactured by Pall Corp.; LST1 and LCR4 manufactured by MacoPharma Co., Ltd.; IMUGARD III manufactured by Terumo Corp. The results of the measurements are summarized and shown in Table 1 and FIG. 3. In FIG. 3, dashed lines indicate kx=0.5, kx=2.0, ky/kx=0.5 and ky/kx=1.5.

TABLE 1

| Brand Name | | Vertical permeation coefficient (kx) ($\times 10^{-12}$ m²) | Horizontal permeation coefficient (ky) ($\times 10^{-12}$ m²) | Horizontal permeation coefficient/vertical permeation coefficient (ky/kx) |
|---|---|---|---|---|
| ASAHIKASEI MEDICAL | RZ-2000 | 1.7 | 4.2 | 2.5 |
| | RS-2000 | 1.4 | 3.0 | 2.1 |
| | R-500 (II) | 2.1 | 3.5 | 1.5 |
| | Pure RC | 1.1 | 2.7 | 2.5 |
| | Flex RC | 1.2 | 2.3 | 2.1 |
| PALL | RCM1 | 0.8 | 6.5 | 8.2 |
| | RCXL1 | 2.3 | 3.1 | 1.4 |
| | WBF2 | 1.6 | 2.9 | 1.8 |
| | WBF3 | 1.6 | 4.4 | 2.7 |
| | BPF4 | 0.8 | 2.2 | 2.7 |
| MACO PHARMA | LST1 | 3.0 | 7.0 | 2.4 |
| | LCR4 | 2.8 | 5.1 | 1.9 |
| TERUMO | IMUGARD III | 3.0 | 2.8 | 0.9 |

INDUSTRIAL APPLICABILITY

The leukocyte-removing method and filter of the present invention are very useful for removing leukocytes from blood which is mainly used for transfusion. It is also useful as a filter used for leukocyte-removing treatment by extracorporeal circulation of blood.

The invention claimed is:
1. A method for removing leukocytes from a leukocyte-containing liquid comprising:
   flowing a leukocyte-containing liquid through a leukocyte-removing filter,
   wherein the leukocyte-removing filter comprises:
      a container having a liquid inlet and outlet; and
      a porous filter material packed in the container, wherein the porous filter material has a permeation coefficient (kx) in the direction vertical to the filtration surface of $0.5 \times 10^{-12}$ m² to $2.0 \times 10^{-12}$ m² and a ratio (ky/kx) of a permeation coefficient (ky) in the direction parallel to the filtration surface to the permeation coefficient (kx) of 0.5 to 1.5; wherein the permeation coefficients (kx) and (ky) are calculated by using equation I:

$$k = (dt/dp) \times \mu \times v \quad \text{(I)};$$

wherein dt is the thickness of the porous filter material, v is the air flow rate, μ is the viscosity of the air, and dp is the pressure drop to be determined, wherein the container includes an inlet-side container having a liquid inlet and an outlet-side container having a liquid outlet, and wherein the inlet-side container and the outlet-side container sandwich the leukocyte-removing filter material directly or through a support to divide the inside of the filter into two compartments.

2. The method for removing leukocytes according to claim 1, wherein the permeation coefficient (kx) of the porous filter material is $1.0 \times 10^{-12}$ m$^2$ to $2.0 \times 10^{-12}$ m$^2$ and the permeation coefficient (ky) is $1.0 \times 10^{-12}$ m$^2$ to $3.0 \times 10^{-12}$ m$^2$.

3. The method for removing leukocytes according to claim 1, wherein the porous filter material is a nonwoven fabric.

4. A leukocyte-removing filter for removing leukocytes from a leukocyte-containing liquid comprising a container having a liquid inlet and outlet and a porous filter material packed in the container, wherein the porous filter material has a permeation coefficient (kx) in the direction vertical to the filtration surface of $0.5 \times 10^{-12}$ m$^2$ to $2.0 \times 10^{-12}$ m$^2$ and a ratio (ky/kx) of a permeation coefficient (ky) in the direction parallel to the filtration surface to the permeation coefficient (kx) of 0.5 to 1.5, wherein the permeation coefficients (kx) and (ky) are calculated by using equation I: $k=(dt/dp) \times \mu \times v$ (I); wherein dt is the thickness of the porous filter material, v is the air flow rate, μ is the viscosity of the air, and dp is the pressure drop to be determined;

wherein the container includes an inlet-side container having a liquid inlet and an outlet-side container having a liquid outlet, and wherein the inlet-side container and the outlet-side container sandwich the leukocyte-removing filter material directly or through a support to divide the inside of the filter into two compartments.

5. The leukocyte-removing filter according to claim 4, wherein the permeation coefficient (kx) of the porous filter material is $1.0 \times 10^{-12}$ m$^2$ to $2.0 \times 10^{-12}$ m$^2$ and the permeation coefficient (ky) is $1.0 \times 10^{-12}$ m$^2$ to $3.0 \times 10^{-12}$ m$^2$.

6. The leukocyte-removing filter according to claim 4, wherein the porous filter material is a nonwoven fabric.

7. The method for removing leukocytes according to claim 2, wherein the porous filter material is a nonwoven fabric.

8. The leukocyte-removing filter according to claim 5, wherein the porous filter material is a nonwoven fabric.

9. The method for removing leukocytes according to claim 1, wherein open spaces of 1 mm or more are provided on the inlet side and/or the outlet side in the direction vertical to the filtration surface.

10. The leukocyte-removing filter according to claim 4, wherein open spaces of 1 mm or more are provided on the inlet side and/or the outlet side in the direction vertical to the filtration surface.

11. The method for removing leukocytes according to claim 1, wherein the container is a flexible container.

12. The leukocyte-removing filter according to claim 4, wherein the container is a flexible container.

13. The method for removing leukocytes according to claim 1, wherein a post filter material is disposed downstream of the porous filter material.

14. The leukocyte-removing filter according to claim 4, wherein a post filter material is disposed downstream of the porous filter material.

15. The method for removing leukocytes according to claim 13, wherein the post filter material has protrusions.

16. The leukocyte-removing filter according to claim 14, wherein the post filter material has protrusions.

17. The method for removing leukocytes according to claim 1, wherein an inner surface of the outlet-side container is provided with concavities and convexities.

18. The leukocyte-removing filter according to claim 4, wherein an inner surface of the outlet-side container is provided with concavities and convexities.

19. The method for removing leukocytes according to claim 1, wherein the container is a hard container.

20. The leukocyte-removing filter according to claim 4, wherein the container is a hard container.

21. The method for removing leukocytes according to claim 1, wherein the container is a planar-shaped container.

22. The leukocyte-removing filter according to claim 4, wherein the container is a planar-shaped container.

23. The method for removing leukocytes according to claim 1, wherein the filling rate of the porous filter material is 0.05 to 0.30.

24. The leukocyte-removing filter according to claim 4, wherein the filling rate of the porous filter material is 0.05 to 0.30.

25. The method for removing leukocytes according to claim 1, wherein the porous filter material has a permeation coefficient (kx) of $0.8 \times 10^{-12}$ m$^2$ to $2.0 \times 10^{-12}$ m$^2$, and wherein the leukocyte-removing filter is structured and arranged to remove leukocytes from a leukocyte-containing liquid and to allow erythrocytes to pass from the liquid.

26. The leukocyte-removing filter according to claim 4, wherein the porous filter material has a permeation coefficient (kx) of $0.8 \times 10^{-12}$ m$^2$ to $2.0 \times 10^{-12}$ m$^2$, and wherein the leukocyte-removing filter is structured and arranged to remove leukocytes from a leukocyte-containing liquid and to allow erythrocytes to pass from the liquid.

* * * * *